United States Patent
Iguchi et al.

(10) Patent No.: US 12,378,513 B2
(45) Date of Patent: Aug. 5, 2025

(54) SCAFFOLD MATERIAL FOR CELL CULTURE AND CELL CULTURE CONTAINER

(71) Applicant: SEKISUI CHEMICAL CO., LTD., Osaka (JP)

(72) Inventors: Hiroki Iguchi, Osaka (JP); Yuuta Nakamura, Osaka (JP); Ryoma Ishii, Osaka (JP); Yuuhei Arai, Osaka (JP); Satoshi Haneda, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 930 days.

(21) Appl. No.: 17/599,349

(22) PCT Filed: Mar. 27, 2020

(86) PCT No.: PCT/JP2020/014012
§ 371 (c)(1),
(2) Date: Sep. 28, 2021

(87) PCT Pub. No.: WO2020/203768
PCT Pub. Date: Oct. 8, 2020

(65) Prior Publication Data
US 2022/0177825 A1   Jun. 9, 2022

(30) Foreign Application Priority Data

Mar. 29, 2019   (JP) ................. 2019-068404

(51) Int. Cl.
C12M 1/12        (2006.01)
(52) U.S. Cl.
CPC .................. C12M 25/14 (2013.01)
(58) Field of Classification Search
None
See application file for complete search history.

(56) References Cited

U.S. PATENT DOCUMENTS 3,910,819 A * 10/1975 Rembaum ................ C12N 1/38
                                                           435/402
4,036,693 A *  7/1977 Levine ................... C12M 25/16
                                                           435/403
(Continued)

FOREIGN PATENT DOCUMENTS

CA   2226133 A1 *  1/1998
CA   2226133      7/1998
(Continued)

OTHER PUBLICATIONS

International Search Report issued Jun. 23, 2020 in International (PCT) Application No. PCT/JP2020/014012.
(Continued)

*Primary Examiner* — Peter A Salamon
(74) *Attorney, Agent, or Firm* — Wenderoth, Lind & Ponack, L.L.P.

(57) ABSTRACT

A scaffold material for cell culture having excellent cell colonization is provided. A scaffold material for cell culture according to the present invention includes a synthetic resin having a main chain and a graft chain, wherein the graft chain has a polydentate hydrogen-bonding group represented by the following formula (1) in a side chain: *—R-$(A_i)_n$ (1) wherein R represents a group having 50 or less carbon atoms, $A_i$ represents an amino group, a carboxyl group, a hydroxyl group, a sulfone group, an imino group, or a thiol group, i represents a natural number, n represents an integer of two or more and four or less, and * represents a bonding position with another atom constituting the graft chain; and $A_i$ may be identical or different from each other.

19 Claims, 1 Drawing Sheet

(56) References Cited

U.S. PATENT DOCUMENTS

| | | | |
|---|---|---|---|
| 4,537,790 A * | 8/1985 | Horodniceanu | C12N 5/0068 |
| | | | 435/402 |
| 2008/0249204 A1* | 10/2008 | Haring | C09D 7/65 |
| | | | 525/308 |
| 2009/0312492 A1 | 12/2009 | Ruslim et al. | |
| 2014/0099695 A1* | 4/2014 | Furuta | C12M 41/36 |
| | | | 435/308.1 |
| 2014/0134734 A1 | 5/2014 | Lin et al. | |
| 2014/0178992 A1 | 6/2014 | Nakashima et al. | |
| 2015/0240067 A1 | 8/2015 | Nagai et al. | |
| 2018/0298178 A1 | 10/2018 | Sato et al. | |
| 2020/0130338 A1 | 4/2020 | Ishikawa et al. | |
| 2020/0139679 A1 | 5/2020 | Ishikawa et al. | |
| 2020/0362289 A1 | 11/2020 | Haneda et al. | |
| 2020/0370009 A1 | 11/2020 | Haneda et al. | |

FOREIGN PATENT DOCUMENTS

| | | |
|---|---|---|
| CN | 101627057 | 1/2010 |
| CN | 103502425 | 1/2014 |
| CN | 103597068 | 2/2014 |
| CN | 103805510 | 5/2014 |
| CN | 108779338 | 11/2018 |
| EP | 0 852 952 | 12/1997 |
| JP | 6-339367 | 12/1994 |
| JP | 10-231373 | 9/1998 |
| JP | 2006-314285 | 11/2006 |
| JP | 2010-220581 | 10/2010 |
| JP | 2010-252631 | 11/2010 |
| JP | 2011-254719 | 12/2011 |
| JP | 2012-165730 | 9/2012 |
| JP | 2017-23008 | 2/2017 |
| JP | 2019-4745 | 1/2019 |
| KR | 10-2014-0128124 | 11/2014 |
| WO | 2007/090102 | 8/2007 |
| WO | 2014/050746 | 4/2010 |
| WO | 2019/021999 | 1/2019 |
| WO | 2019/022000 | 1/2019 |
| WO | 2019/131978 | 7/2019 |

OTHER PUBLICATIONS

Hongsheng Zhao et al., "Study on Polyether Biomaterials as Macroporous Carriers," Journal of Functional Polymers, vol. 18, No. 3, East China University Of Science and Technology, Sep. 2005, pp. 361-367, with English Abstract provided on p. 367. English abstract only.

International Preliminary Report on Patentability issued Sep. 28, 2021 in International (PCT) Application No. PCT/JP2020/014012.

Extended European Search Report issued Mar. 22, 2023 in corresponding European Patent Application No. 20783167.8.

Ding Matai, "Introduction to Materials Chemistry," Xiamen University Press, Jan. 1996, pp. 306-309, with English-language translation.

* cited by examiner

SCAFFOLD MATERIAL FOR CELL CULTURE AND CELL CULTURE CONTAINER

TECHNICAL FIELD

The present invention relates to a scaffold material for cell culture used for culturing a cell. The present invention also relates to a cell culture container using the scaffold material for cell culture.

BACKGROUND ART

Animal cells such as a human, a mouse, a rat, a pig, a cow and a monkey are used in research and development in an academic field, a drug discovery field, a regenerative medicine field and the like. As a scaffold material used for culturing an animal cell, adhesive proteins such as laminin and vitronectin, and natural polymer materials such as Matrigel derived from mouse sarcoma are used.

Furthermore, as shown in Patent Documents 1 to 3 below, scaffold materials using synthetic resins are also known.

Patent Document 1 below discloses a carrier for cell culture composed of a molded product made of a polyvinyl acetal compound or a molded product made of the polyvinyl acetal compound and a water-soluble polysaccharide, wherein the polyvinyl acetal compound has a degree of acetalization of 20 to 60 mol %.

Furthermore, Patent Document 2 below discloses a composition (scaffold material) containing a first fiber polymer scaffold material, wherein fibers of the first fiber polymer scaffold material are aligned. Aliphatic polyester and the like are used as a material of the fiber polymer.

Furthermore, Patent Document 3 below discloses a method of culturing a cell to maintain an undifferentiated state of a pluripotent stem cell, which includes the step of culturing the pluripotent stem cell on an incubator having a surface coated with a polyrotaxane block copolymer.

RELATED ART DOCUMENTS

Patent Documents

Patent Document 1: JP 2006-314285 A
Patent Document 2: WO 2007/090102 A1
Patent Document 3: JP 2017-023008 A

SUMMARY OF THE INVENTION

Problems to be Solved by the Invention

In culturing an animal cell, a cell cluster may be seeded and cultured on a scaffold material. By using a natural polymer material as the scaffold material, cell colonization after seeding can be enhanced. However, the natural polymer material is expensive, has large lot-to-lot variation due to a naturally derived substance, and there is a safety concern due to an animal-derived component.

On the other hand, the scaffold materials using synthetic resins as described in Patent Documents 1 to 3 are less expensive than the scaffold material using the natural polymer material, have less lot-to-lot variation, and are excellent in safety. However, in the scaffold materials using the conventional synthetic resins as described in Patent Documents 1 to 3, there is a problem that affinity between the synthetic resin and a cell is low, the synthetic resin swells excessively because high hydrophilicity is used, and therefore a seeded cell cluster easily is detached from the scaffold material during culturing, and cell colonization is low.

An object of the present invention is to provide a scaffold material for cell culture having excellent cell colonization. Another object of the present invention is to provide a cell culture container using the scaffold material for cell culture.

Means for Solving the Problems

According to a broad aspect of the present invention, there is provided a scaffold material for cell culture including a synthetic resin having a main chain and a graft chain, the graft chain having a polydentate hydrogen-bonding group represented by the following formula (1) in a side chain:

[Chemical 1]

$$*-R-(A_i)_n \qquad (1)$$

wherein R represents a group having 50 or less carbon atoms, $A_i$ represents an amino group, a carboxyl group, a hydroxyl group, a sulfone group, an imino group, or a thiol group, i represents a natural number, n represents an integer of two or more and four or less, and * represents a bonding position with another atom constituting the graft chain; and $A_i$ may be identical or different from each other.

In a specific aspect of the scaffold material for cell culture according to the present invention, the polydentate hydrogen-bonding group is a polydentate hydrogen-bonding group represented by the following formula (2), the following formula (3), or the following formula (4):

[Chemical 2]

(2)

wherein $R_1$ represents a group having a cyclic skeleton and having 50 or less carbon atoms, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other,

[Chemical 3]

(3)

wherein $R_1$ represents a group having a cyclic skeleton and having 50 or less carbon atoms, $R_2$ represents a boron atom, a phosphorus atom, a silicon atom, a nitrogen atom, or a metal atom, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other,

[Chemical 4]

(4)

wherein $R_3$ represents a group having a chain skeleton and having 50 or less carbon atoms, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other.

In a specific aspect of the scaffold material for cell culture according to the present invention, the polydentate hydrogen-bonding group is a polydentate hydrogen-bonding group represented by the formula (2) or the formula (3).

In a specific aspect of the scaffold material for cell culture according to the present invention, the polydentate hydrogen-bonding group has two or more functional groups of at least one kind selected from the group consisting of an amino group, a carboxyl group, and a hydroxyl group.

In a specific aspect of the scaffold material for cell culture according to the present invention, the polydentate hydrogen-bonding group has at least one skeleton selected from the group consisting of a catechol skeleton, a phenylenediamine skeleton, a phenylboronic acid skeleton, a naphthaleneboronic acid skeleton, a glycerol skeleton, an ethylene glycol skeleton, and a glycine derivative skeleton.

In a specific aspect of the scaffold material for cell culture according to the present invention, the scaffold material for cell culture does not substantially contain an animal-derived raw material.

In a specific aspect of the scaffold material for cell culture according to the present invention, a rate of a structural unit having the polydentate hydrogen-bonding group to 100 mol % of all structural units of the synthetic resin is 1 mol % or more and 30 mol % or less.

In a specific aspect of the scaffold material for cell culture according to the present invention, the synthetic resin is a polyvinyl alcohol derivative or a poly(meth)acrylic ester derivative.

In a specific aspect of the scaffold material for cell culture according to the present invention, the synthetic resin has a polyvinyl acetal skeleton or a poly(meth)acrylic ester skeleton.

In a specific aspect of the scaffold material for cell culture according to the present invention, the synthetic resin has the polyvinyl acetal skeleton.

According to a broad aspect of the present invention, there is provided a cell culture container including a container body; and the above-mentioned scaffold material for cell culture, the scaffold material for cell culture being disposed on a surface of the container body.

Effect of the Invention

According to the present invention, it is possible to provide a scaffold material for cell culture having excellent cell colonization. Furthermore, according to the present invention, it is possible to provide a cell culture container using the scaffold material for cell culture.

MODES FOR CARRYING OUT THE INVENTION

Hereinafter, the present invention is described in detail.
(Polydentate Hydrogen-Bonding Group)

The scaffold material for cell culture according to the present invention is used for culturing a cell. The scaffold material for cell culture according to the present invention includes a synthetic resin having a polydentate hydrogen-bonding group represented by the following formula (1) (hereinafter, may be abbreviated as "polydentate hydrogen-bonding group") in a side chain of a graft chain. The polydentate hydrogen-bonding group is a group capable of forming two or more hydrogen bonds.

[Chemical 4]

$$*\text{—}R\text{-}(A_i)_n \qquad (1)$$

wherein R represents a group having 50 or less carbon atoms, $A_i$ represents an amino group, a carboxyl group, a hydroxyl group, a sulfone group, an imino group, or a thiol group, i represents a natural number, n represents an integer of two or more and four or less, and * represents a bonding position with another atom constituting the graft chain; and $A_i$ may be identical or different from each other.

In the formula (1), R may be a group having a cyclic skeleton or a group having a chain skeleton. From the viewpoint of further enhancing cell colonization, it is preferable that R is a group having a cyclic skeleton in the formula (1).

From the viewpoint of exerting the effect of the present invention even more effectively, a carbon number of R in the formula (1) is preferably 45 or less, more preferably 30 or less, and further preferably 20 or less.

In the formula (1), $A_i$ is an amino group, a carboxyl group, a hydroxyl group, a sulfone group, an imino group, or a thiol group. From the viewpoint of exerting the effect of the present invention even more effectively, in the formula (1), $A_i$ is preferably at least one functional group selected from the group consisting of an amino group, a carboxyl group, and a hydroxyl group, more preferably at least one functional group selected from the group consisting of an amino group and a hydroxyl group, and further preferably a hydroxyl group.

From the viewpoint of exerting the effect of the present invention even more effectively, the polydentate hydrogen-bonding group represented by the formula (1) has preferably one or more functional groups selected from the group consisting of an amino group, a carboxyl group, and a hydroxyl group, and more preferably two or more functional groups. From the viewpoint of exerting the effect of the present invention further more effectively, the polydentate hydrogen-bonding group represented by the formula (1) has preferably one or more functional groups selected from the group consisting of an amino group and a hydroxyl group, more preferably one or more hydroxyl groups, and further preferably two or more hydroxyl groups.

In the formula (1), n is an integer of two or more and four or less. From the viewpoint of exerting the effect of the present invention even more effectively, in the formula (1), n is preferably two or three and more preferably two.

Therefore, the polydentate hydrogen-bonding group preferably has two or three $A_i$, and more preferably two.

Furthermore, from the viewpoint of exerting the effect of the present invention even more effectively, in the formula (1), the number of atoms existing between any $A_i$ and the adjacent $A_i$ is preferably four or less, more preferably three or less, and further preferably two or one.

In the formula (1), the number of atoms existing between any $A_i$ and the adjacent $A_i$ means the number of atoms connecting these two $A_i$ at the shortest. For example, the fact that the number of atoms existing between any $A_i$ and the adjacent $A_i$ is two means that the atom to which one $A_i$ is bonded and the atom to which the other $A_i$ is bonded are bonded. Furthermore, for example, the fact that the number of atoms existing between any $A_i$ and the adjacent $A_i$ is one means that one $A_i$ and the other $A_i$ are bonded to the same atom.

From the viewpoint of exerting the effect of the present invention even more effectively, the polydentate hydrogen-bonding group represented by the formula (1) is preferably the polydentate hydrogen-bonding group represented by the following formula (2), the following formula (3), or the following formula (4), and more preferably the polydentate hydrogen-bonding group represented by the following formula (2) or the following formula (3).

[Chemical 5]

(2)

wherein $R_1$ represents a group having a cyclic skeleton and having 50 or less carbon atoms, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other.

In the formula (2), examples of $R_1$ include a group having an aromatic ring and a group having an aliphatic ring. The aliphatic ring may have a double bond in part of the ring.

Examples of the group having an aromatic ring include a group having a phenyl skeleton, a group having a naphthyl skeleton, and a group having an anthryl skeleton. From the viewpoint of enhancing the adhesiveness with a cell, the group having an aromatic ring is preferably a group having a phenyl skeleton or a group having a naphthyl skeleton, and more preferably the group having a phenyl skeleton.

Examples of the group having an aliphatic ring include a cyclobutyl group, a cyclopentyl group and a cyclohexyl group. From the viewpoint of enhancing the adhesiveness to a cell, it is preferable that the group having an aliphatic ring is a cyclopentyl group or a cyclohexyl group.

Furthermore, from the viewpoint of exerting the effect of the present invention even more effectively, the number of atoms existing between $A_1$ and $A_2$ in the formula (2) is preferably four or less, more preferably three or less, further preferably two.

In the formula (2), the number of atoms existing between $A_1$ and $A_2$ means the number of atoms connecting $A_1$ and $A_2$ at the shortest. For example, the fact that the number of atoms existing between $A_1$ and $A_2$ is two means that the atom to which $A_1$ is bonded and the atom to which $A_2$ is bonded are bonded.

From the viewpoint of exerting the effect of the present invention even more effectively, in the formula (2), $A_1$ and $A_2$ are particularly preferably bonded to two adjacent atoms constituting the cyclic skeleton of $R_1$, respectively.

Examples of the polydentate hydrogen-bonding group represented by the formula (2) include a group having a catechol skeleton and a group having a phenylenediamine skeleton. From the viewpoint of enhancing cell colonization, it is preferable that the polydentate hydrogen-bonding group represented by the formula (2) is the group having a catechol skeleton.

[Chemical 6]

(3)

wherein $R_1$ represents a group having a cyclic skeleton and having 50 or less carbon atoms, $R_2$ represents a boron atom, a phosphorus atom, a silicon atom, a nitrogen atom, or a metal atom, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other.

In the formula (3), examples of the metal atom include a platinum atom and an aluminum atom.

From the viewpoint of exerting the effect of the present invention even more effectively, in the formula (3), $R_2$ is preferably a boron atom, a phosphorus atom, a silicon atom, or a nitrogen atom, and more preferably a boron atom.

Examples of the polydentate hydrogen-bonding group represented by the formula (3) include a group having a phenylboronic acid skeleton and a group having a naphthaleneboronic acid skeleton. From the viewpoint of enhancing cell colonization, it is preferable that the polydentate hydrogen-bonding group represented by the formula (3) is the group having a phenylboronic acid skeleton.

[Chemical 7]

(4)

wherein $R_3$ represents a group having a chain skeleton and having 50 or less carbon atoms, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other.

In the formula (4), $R_3$ may be a group having a chain skeleton with a linear chain or a group having a chain skeleton with a branched chain. Examples of the above $R_3$ include an alkyl group having 50 or less carbon atoms.

Furthermore, from the viewpoint of exerting the effect of the present invention even more effectively, the number of atoms existing between $A_1$ and $A_2$ in the formula (4) is preferably four or less, more preferably three or less, further preferably two.

In the formula (4), the number of atoms existing between $A_1$ and $A_2$ means the number of atoms connecting $A_1$ and $A_2$ at the shortest. For example, the fact that the number of atoms existing between $A_1$ and $A_2$ is two means that the atom to which $A_1$ is bonded and the atom to which $A_2$ is bonded are bonded.

Examples of the polydentate hydrogen-bonding group represented by the formula (4) include a group having a glycerol skeleton, a group having an ethylene glycol skeleton, and a glycine derivative skeleton (a structure in which a carboxyl group and an amino group are bonded to the terminal carbon).

From the viewpoint of exerting the effects of the present invention even more effectively, it is preferable that the polydentate hydrogen-bonding group has a cyclic skeleton. Examples of the cyclic skeleton include an aromatic ring skeleton and an alicyclic skeleton. The alicyclic skeleton may be a saturated alicyclic skeleton having no double bond, or an unsaturated alicyclic skeleton having a double bond. Furthermore, the cyclic skeleton may contain an atom other than a carbon atom as an atom constituting the cyclic skeleton.

The number of atoms constituting the cyclic skeleton is preferably five or more, more preferably 10 or more, preferably 40 or less, and more preferably 30 or less.

From the viewpoint of exerting the effects of the present invention even more effectively, it is preferable that the polydentate hydrogen-bonding group has at least one skeleton selected from the group consisting of a catechol skeleton, a phenylenediamine skeleton, a phenylboronic acid skeleton, a naphthaleneboronic acid skeleton, a glycerol skeleton, an ethylene glycol skeleton, and a glycine derivative skeleton.

When the polydentate hydrogen-bonding group has the cyclic skeleton, a hydrogen-bonding functional group ($A_i$) may or may not be directly bonded to the atom constituting the cyclic skeleton.

When the polydentate hydrogen-bonding group has a cyclic skeleton, it is preferable that the polydentate hydrogen-bonding group has a hydrogen-bonding functional group directly bonded to the cyclic skeleton, or has a hydrogen-bonding functional group bonded to a cyclic skeleton with one atom therebetween. In this case, the effect of the present invention can be more effectively exerted.

(Synthetic Resin X)

The scaffold material for cell culture according to the present invention contains a synthetic resin having a main chain and a graft chain, wherein the graft chain has a polydentate hydrogen-bonding group represented by the formula (1) in a side chain (hereinafter, may be referred to as a "synthetic resin X"). Therefore, the scaffold material for cell culture according to the present invention contains the synthetic resin X. The synthetic resin X may be a composite resin. As the synthetic resin X, only one kind may be used, or two or more kinds may be used in combination. Furthermore, the synthetic resin X may have only one kind of the polydentate hydrogen-bonding group, or may have two or more kinds.

The polydentate hydrogen-bonding group may be directly bonded to the main chain of the graft chain, or may be bonded to the main chain of the graft chain with another group therebetween.

The synthetic resin X can be synthesized, for example, by the following method (1) or (2).

(1) A method of graft-polymerizing a monomer having a polydentate hydrogen-bonding group or a mixed monomer of a monomer having a polydentate hydrogen-bonding group and a monomer having no polydentate hydrogen-bonding group to a polymer of the main chain.

(2) A method in which a polymer having a polydentate hydrogen-bonding group in a side chain is bonded to a polymer of the main chain in a branched manner by condensation or the like.

Examples of the monomer having a polydentate hydrogen-bonding group and the monomer having no polydentate hydrogen-bonding group include a vinyl compound, a (meth)acrylic monomer, and a maleimide compound. As the monomer, only one kind may be used, or two or more kinds may be used in combination. When synthesizing the synthetic resin X, it is preferable to use at least one kind of monomer having a polydentate hydrogen-bonding group represented by the formula (1).

Examples of the monomer having the polydentate hydrogen-bonding group include a monomer both having a (meth)acryloyl group and having two or more functional groups of at least one kind selected from the group consisting of an amino group, a carboxyl group, a hydroxyl group, a sulfone group, an imino group, and a thiol group. Examples of such a monomer having a polydentate hydrogen-bonding group include dopamine acrylamide, 4-methacrylamide phenylboronic acid, glycerol monomethacrylate, DL-2-allylglycine, vinyl catechol, 3-methacrylamide phenylboronic acid, and 2-[2-hydroxy-5-[2-(methacryloyloxy)ethyl]phenyl]-2H-benzotriazole.

Since the scaffold material for cell culture according to the present invention contains the synthetic resin X having the polydentate hydrogen-bonding group, the polydentate hydrogen-bonding group and a cell (for example, a membrane protein, a phospholipid, a sugar chain, a sugar protein, an extracellular matrix, and an adhesive protein) can be well hydrogen-bonded, and the number of the hydrogen bonds can be increased. Therefore, in the present invention, the affinity between the synthetic resin X and a cell is enhanced, and as a result, the cell is less likely to be detached from the scaffold material for cell culture, and cell colonization can be enhanced.

Furthermore, the scaffold material for cell culture according to the present invention is less expensive than the conventional cell scaffold material using a natural polymer, has less lot-to-lot variation, and is excellent in safety.

Figure 2:
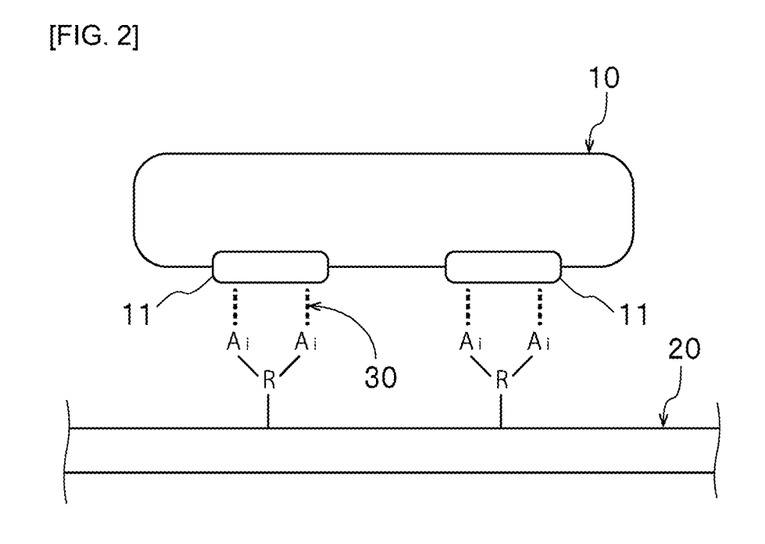
FIG. 2 is a schematic diagram for explaining an estimation mechanism for improving cell colonization when a cell is cultured using the scaffold material for cell culture according to the present invention.

FIG. 2 is a schematic diagram for explaining an estimation mechanism in which cell colonization is improved when a cell is cultured using the scaffold material for cell culture according to the present invention.

As shown in FIG. 2, a cell 10 has a substance 11 capable of forming a hydrogen bond, such as a membrane protein and a compound with a sugar chain on the cell membrane. Furthermore, a scaffold material for cell culture 20 according to the present invention contains the synthetic resin X having the polydentate hydrogen-bonding group. When a cell is seeded on a surface of the scaffold material for cell culture 20, two or more hydrogen bonds 30 are formed per one polydentate hydrogen-bonding group between the polydentate hydrogen-bonding group and the membrane protein and sugar chain existing in the cell membrane. As a result, a strong bond is formed between the cell 10 and the scaffold material for cell culture 20 with the polydentate hydrogen-bonding group therebetween. Therefore, it is considered that the adhesiveness between a cell and a scaffold material for cell culture is improved, and as a result, cell colonization is improved.

Furthermore, in the present invention, since the synthetic resin X has the polydentate hydrogen-bonding group in a side chain of a graft chain, the adhesiveness to a cell is likely to improve. Although the details of this mechanism are unknown, a plurality of the polydentate hydrogen-bonding groups arranged on the same graft chain form a cluster, and a strong bond is formed between a cell and the scaffold material for cell culture with the polydentate hydrogen-bonding group therebetween.

Examples of the synthetic resin X include a polyolefin derivative, a polyether derivative, a polyvinyl alcohol derivative, a polyester derivative, a poly(meth)acrylic ester derivative, an epoxy resin derivative, a polyamide derivative, a polyimide derivative, a polyurethane derivative, a polycarbonate derivative, a cellulose derivative, and a polypeptide derivative.

From the viewpoint of exerting the effects of the present invention effectively, it is preferable that the synthetic resin X is the polyvinyl alcohol derivative or the poly(meth)acrylic ester derivative. The polyvinyl alcohol derivative is a synthetic resin synthesized by using at least a vinyl alcohol as a monomer. The poly(meth)acrylic ester derivative is a synthetic resin synthesized by using at least an acrylic ester as a monomer.

It is preferable that the polyvinyl alcohol derivative is a resin having a polyvinyl acetal skeleton.

Therefore, it is preferable that the synthetic resin X has the polyvinyl acetal skeleton or the poly(meth)acrylic ester skeleton. In this case, the synthetic resin X may be a resin having a polyvinyl acetal skeleton, may be a resin having a poly(meth)acrylic ester skeleton, or may be a resin having both a polyvinyl acetal skeleton and a poly(meth)acrylic ester skeleton.

From the viewpoint of exerting the effects of the present invention effectively, it is preferable that the synthetic resin X is the resin having a polyvinyl acetal skeleton or the resin having both a polyvinyl acetal skeleton and a poly(meth)acrylic ester skeleton. It is preferable that the synthetic resin X is the resin having at least a polyvinyl acetal skeleton.

A rate of a structural unit having the polydentate hydrogen-bonding group to 100 mol % of all structural units of the synthetic resin X (content of the structural unit having the polydentate hydrogen-bonding group) is preferably 1 mol % or more, more preferably 5 mol % or more, preferably 30 mol % or less, and more preferably 20 mol % or less. When the above-mentioned rate is equal to or higher than the lower limit and equal to or lower than the upper limit, the effect of the present invention can be even more effectively exerted. The structural unit having the polydentate hydrogen-bonding group is, for example, a structural unit derived from a monomer having a polydentate hydrogen-bonding group.

The rate of the structural unit having the polydentate hydrogen-bonding group can be measured by $^1$H-NMR (nuclear magnetic resonance spectrum).

The content of the synthetic resin X in 100% by weight of the scaffold material for cell culture is preferably 70% by weight or more, more preferably 75% by weight or more, still more preferably 80% by weight or more, and particularly preferably 90% by weight or more, and most preferably 100% by weight (total amount). Therefore, the scaffold material for cell culture is most preferably the synthetic resin X. When the content of the synthetic resin X is equal to or higher than the lower limit, the effect of the present invention can be even more effectively exerted.

<Synthetic Resin X with Polyvinyl Acetal Skeleton>

It is preferable that a scaffold material for cell culture contains a synthetic resin X having a polyvinyl acetal skeleton.

In the present specification, a "synthetic resin X having a polyvinyl acetal skeleton" may be referred to as a "polyvinyl acetal resin X".

Therefore, the polyvinyl acetal resin X is a resin having a polyvinyl acetal skeleton and a polydentate hydrogen-bonding group.

The polyvinyl acetal resin X has an acetal group, an acetyl group, and a hydroxyl group in a side chain. Furthermore, the polyvinyl acetal resin X has the polydentate hydrogen-bonding group.

When synthesizing the polyvinyl acetal resin X, at least a step of acetalizing a polyvinyl alcohol with an aldehyde is provided.

The average degree of polymerization of the polyvinyl acetal resin X or the polyvinyl acetal resin (before polymerization of a monomer having a polydentate hydrogen-bonding group) is preferably 100 or more, more preferably 200 or more, further preferably 500 or more, particularly preferably 1500 or more, preferably 6000 or less, more preferably 3000 or less, and further preferably 2500 or less. When the average degree of polymerization is equal to or higher than the lower limit, swelling due to a liquid medium can be effectively suppressed, so that the strength of the scaffold material for cell culture can be maintained well. Therefore, cell proliferation can be enhanced. Furthermore, when the average degree of polymerization is equal to or lower than the upper limit, handleability can be improved and formability of the scaffold material for cell culture can be improved.

The number average molecular weight (Mn) of the polyvinyl acetal resin X or the polyvinyl acetal resin (before polymerization of a monomer having a polydentate hydrogen-bonding group) is preferably 10000 or more, and preferably 600000 or less. The weight average molecular weight (Mw) of the polyvinyl acetal resin X or the polyvinyl acetal resin (before polymerization of a monomer having a polydentate hydrogen-bonding group) is preferably 2000 or more, and preferably 1200000 or less. Furthermore, in the polyvinyl acetal resin X or the polyvinyl acetal resin (before polymerization of a monomer having a polydentate hydrogen-bonding group), the ratio (Mw/Mn) of the weight average molecular weight (Mw) to the number average molecular weight (Mn) is preferably 2.0 or more, and preferably 40 or less. When the above Mn, the above Mw, and the above Mw/Mn are equal to or higher than the lower limit, and equal to or lower than the upper limit, the strength of the scaffold material for cell culture can be increased.

The degree of acetalization of the polyvinyl acetal resin X or the polyvinyl acetal resin (before polymerization of a monomer having a polydentate hydrogen-bonding group) (in the case of a polyvinyl butyral resin, the degree of butyralization) is preferably 60 mol % or more, more preferably 65 mol % or more, preferably 90 mol % or less, and more preferably 85 mol % or less. When the degree of acetalization is equal to or higher than the lower limit, cell colonization can be further enhanced, and a cell proliferates efficiently. When the degree of acetalization is equal to or lower than the upper limit, solubility in a solvent can be improved.

The degree of acetylation (acetyl group amount) of the polyvinyl acetal resin X or the polyvinyl acetal resin (before polymerization of a monomer having a polydentate hydrogen-bonding group) is preferably 0.0001 mol % or more, and preferably 5 mol % or less.

The hydroxyl group content (hydroxyl group amount) of the polyvinyl acetal resin X or the polyvinyl acetal resin (before polymerization of a monomer having a polydentate hydrogen-bonding group) is preferably 1 mol % or more, more preferably 10 mol % or more, preferably 80 mol % or less, and more preferably 60 mol % or less.

The degree of acetalization, the degree of acetylation (acetyl group amount) and the hydroxyl group amount of the polyvinyl acetal resin X or the polyvinyl acetal resin before polymerization of a monomer having a polydentate hydrogen-bonding group can be measured by $^1$H-NMR (nuclear magnetic resonance spectrum).

The polyvinyl acetal resin X can be synthesized, for example, by the following method (1) or (2). (1) A method of graft-polymerizing a monomer having a polydentate hydrogen-bonding group or a mixed monomer of a monomer having a polydentate hydrogen-bonding group and a monomer having no polydentate hydrogen-bonding group to a polyvinyl acetal resin. (2) A method in which a polymer having a polydentate hydrogen-bonding group in a side chain is bonded to a polyvinyl acetal resin like a branch by condensation or the like.

Since it is easy to adjust the degree of acetalization, the content of the hydroxyl group amount and the acetyl group amount, and the like, it is preferable that the polyvinyl acetal resin X is a graft copolymer of a polyvinyl acetal resin and a monomer having a polydentate hydrogen-bonding group. Furthermore, the polyvinyl acetal resin X is more preferably a graft copolymer of the polyvinyl acetal resin, the monomer having a polydentate hydrogen-bonding group, and a monomer other than the monomer having a polydentate hydrogen-bonding group. In this case, since the polydentate hydrogen-bonding group contained in the polyvinyl acetal resin X is likely to bind to a cell, cell colonization can be further enhanced.

Examples of the monomer having a polydentate hydrogen-bonding group include the above-mentioned monomers.

Examples of the monomer other than the monomer having a polydentate hydrogen-bonding group include a vinyl compound having no polydentate hydrogen-bonding group.

Examples of the vinyl compound having no polydentate hydrogen-bonding group include ethylene, allylamine, vinylpyrrolidone, maleic anhydride, maleimide, itaconic acid, (meth)acrylic acid having no polydentate hydrogen-bonding group, and (meth)acrylic ester having no vinylamine and polydentate hydrogen-bonding group. As the vinyl compound having no polydentate hydrogen-bonding group, only one kind may be used, or two or more kinds may be used in combination. A copolymer of the polyvinyl acetal resin and a (meth)acrylic ester is described later.

<Synthetic Resin X Having Poly(Meth)Acrylic Ester Skeleton>

It is preferable that a scaffold material for cell culture contains a synthetic resin X having a poly(meth)acrylic ester skeleton.

In the present specification, a "synthetic resin X having a poly(meth)acrylic ester skeleton" may be referred to as a "poly(meth)acrylic ester resin X".

Therefore, the poly(meth)acrylic ester resin X is a resin having a poly(meth)acrylic ester skeleton and a polydentate hydrogen-bonding group.

The poly(meth)acrylic ester resin X is obtained by polymerizing the (meth)acrylic ester with the monomer having a polydentate hydrogen-bonding group. The poly(meth) acrylic ester resin X may be a resin obtained by copolymerizing the (meth)acrylic ester, the monomer having a polydentate hydrogen-bonding group, and a monomer different from both the (meth)acrylic ester and the monomer having a polydentate hydrogen-bonding group.

Examples of the (meth)acrylic ester include a (meth) acrylic acid alkyl ester, a (meth)acrylic acid cyclic alkyl ester, a (meth)acrylic acid aryl ester, (meth)acrylamides, (meth)acrylic acid polyethylene glycols, and a phosphorylcholine (meth)acrylate.

Examples of the (meth)acrylic acid alkyl ester include methyl(meth)acrylate, ethyl(meth)acrylate, n-propyl(meth) acrylate, isopropyl(meth)acrylate, n-butyl(meth)acrylate, isobutyl(meth)acrylate, t-butyl(meth)acrylate, n-octyl(meth) acrylate, isooctyl(meth)acrylate, 2-ethylhexyl(meth)acrylate, nonyl(meth)acrylate, isononyl(meth)acrylate, decyl (meth)acrylate, isodecyl(meth)acrylate, lauryl(meth) acrylate, stearyl(meth)acrylate, and isotetradecyl(meth) acrylate.

The (meth)acrylic acid alkyl ester may be substituted with a substituent such as an alkoxy group having one to three carbon atoms and a tetrahydrofurfuryl group. Examples of such (meth)acrylic acid alkyl ester include methoxyethyl acrylate and tetrahydrofurfuryl acrylate.

Examples of the (meth)acrylic acid cyclic alkyl ester include cyclohexyl(meth)acrylate and isobornyl(meth)acrylate.

Examples of the (meth)acrylic acid aryl ester include phenyl(meth)acrylate and benzyl(meth)acrylate.

Examples of the (meth)acrylamides include (meth)acrylamide, N-isopropyl(meth)acrylamide, N-tert-butyl(meth) acrylamide, N,N'-dimethyl(meth)acrylamide, (3-(meth) acrylamidepropyl)trimethylammonium chloride, 4-(meth) acryloylmorpholine, 3-(meth)acryloyl-2-oxazolidinone, N-[3-(dimethylamino)propyl](meth)acrylamide, N-(2-hydroxyethyl) (meth)acrylamide, N-methylol(meth)acrylamide, and 6-(meth)acrylamide hexane acid.

Examples of the (meth)acrylate polyethylene glycols include methoxy-polyethylene glycol(meth)acrylate, ethoxy-polyethylene glycol(meth)acrylate, hydroxy-polyethylene glycol(meth)acrylate, methoxy-diethylene glycol (meth)acrylate, and ethoxy-diethylene glycol(meth)acrylate, hydroxy-diethylene glycol(meth)acrylate, methoxy-triethylene glycol(meth)acrylate, ethoxy-triethylene glycol(meth) acrylate, and hydroxy-triethylene glycol(meth)acrylate.

Examples of the phosphorylcholine(meth)acrylate include 2-(meth)acryloyloxyethyl phosphorylcholine.

Examples of the monomer having a polydentate hydrogen-bonding group include the above-mentioned monomers.

Examples of the monomer different from both the (meth) acrylic ester and the monomer having a polydentate hydrogen-bonding group include (meth)acrylic acid, ethylene, and a vinyl ester.

In addition, in the present specification, "(meth)acrylic" means "acrylic" or "methacryl", and "(meth)acrylate" means "acrylate" or "methacrylate".

The number average molecular weight (Mn) of the poly (meth)acrylic ester resin X is preferably 100 or more and preferably 200000 or less. The weight average molecular weight (Mw) of the poly(meth)acrylic ester resin X is preferably 100 or more and preferably 200000 or less.

<Synthetic Resin X Having Polyvinyl Acetal Skeleton and Poly(Meth)Acrylic Ester Skeleton>

It is preferable that a scaffold material for cell culture contains a synthetic resin X having a polyvinyl acetal skeleton and a poly(meth)acrylic ester skeleton. It is preferable that the synthetic resin X is a composite resin having a polyvinyl acetal skeleton and a poly(meth)acrylic ester skeleton.

The synthetic resin X having a polyvinyl acetal skeleton and a poly(meth)acrylic ester skeleton is a resin having a polyvinyl acetal skeleton, a poly(meth)acrylic ester skeleton and a polydentate hydrogen-bonding group.

The synthetic resin X having a polyvinyl acetal skeleton and a poly(meth)acrylic ester skeleton can be synthesized by, for example, appropriately combining the above-mentioned method for synthesizing the polyvinyl acetal resin X and the method for synthesizing the poly(meth)acrylic ester resin X.

It is preferable that the synthetic resin X having a polyvinyl acetal skeleton and a poly(meth)acrylic ester skeleton is the synthetic resin X obtained by graft-copolymerizing the above-mentioned (meth)acrylic ester with the above-mentioned polyvinyl acetal resin.

The number average molecular weight (Mn) of the synthetic resin X having a polyvinyl acetal skeleton and a poly(meth)acrylic ester skeleton is preferably 10000 or more and preferably 600000 or less. The weight average molecular weight (Mw) of the synthetic resin X having a polyvinyl acetal skeleton and a poly(meth)acrylic ester skeleton is preferably 2000 or more and preferably 1200000 or less. Furthermore, in the synthetic resin X having a polyvinyl acetal skeleton and a poly(meth)acrylic ester skeleton, the ratio (Mw/Mn) of the weight average molecular weight (Mw) to the number average molecular weight (Mn) is preferably 2.0 or more and preferably 40 or less. When the above Mn, the above Mw, and the above Mw/Mn are equal to or higher than the lower limit, and equal to or lower than the upper limit, the strength of the scaffold material for cell culture can be increased.

Polymer Other than Synthetic Resin X:

The scaffold material for cell culture may contain a polymer other than the synthetic resin X. Examples of the polymer include a polyolefin resin, a polyether resin, a polyvinyl alcohol resin, a polyester, an epoxy resin, a polyamide resin, a polyimide resin, a polyurethane resin, a polycarbonate resin, a cellulose, and a polypeptide.

From the viewpoint of effectively exerting the effects of the present invention, the smaller the content of the polymer other than the synthetic resin X, the better. The content of the polymer in 100% by weight of the scaffold material for cell culture is preferably 20% by weight or less, more preferably 10% by weight or less, further preferably 5% by weight or less, particularly preferably 1% by weight or less, and most preferably 0% by weight (not contained). Therefore, it is most preferable that the scaffold material for cell culture does not contain the polymer other than the synthetic resin X.

It is preferable that the scaffold material for cell culture according to the present invention does not substantially contain an animal-derived raw material. Since the scaffold material for cell culture does not substantially contain the animal-derived raw material, it is possible to provide a scaffold material for cell culture which has less lot-to-lot variation and is excellent in cost performance and safety. In addition, "does not substantially contain an animal-derived raw material" means that the animal-derived raw material in the scaffold material for cell culture is 3% by weight or less. As for the scaffold material for cell culture according to the present invention, the amount of the animal-derived raw material in the scaffold material for cell culture is preferably 1% by weight or less, and more preferably 0% by weight. That is, it is more preferable that the scaffold material for cell culture does not contain the animal-derived raw material in the scaffold material for cell culture.

(Other Details of Scaffold Material for Cell Culture)

The scaffold material for cell culture according to the present invention is used for culturing a cell. The scaffold material for cell culture according to the present invention is used as a scaffold for a cell when the cell is cultured.

Examples of the cell include animal cells such as a human, a mouse, a rat, a pig, a cow and a monkey. Examples of the cell include a somatic cell, a stem cell, a progenitor cell, and a differentiated cell. The somatic cell may be a cancer cell.

Examples of the stem cell include a mesenchymal stem cell (MSC), an iPS cell, an ES cell, a Muse cell, an embryonal cancer cell, an embryonic germ stem cell, and an mGS cell.

A shape of the scaffold material for cell culture is not particularly limited. The shape of the scaffold material for cell culture may be a membranous form or a particulate form. The membranous form includes a film form and a sheet form.

It is preferable that the scaffold material for cell culture is used for two-dimensional culture (plane culture), three-dimensional culture or suspension culture of a cell, and it is more preferable that the scaffold material is used for two-dimensional culture (plane culture).

Furthermore, the scaffold material for cell culture can also be used as a cell culture carrier (medium) containing the scaffold material for cell culture and a polysaccharide. The polysaccharide is not particularly limited, and a conventionally known polysaccharide can be used. It is preferable that the polysaccharide is a water-soluble polysaccharide.

Furthermore, the scaffold material for cell culture can also be used as a fiber for cell culture including a fiber body and a scaffold material for cell culture disposed on the surface of the fiber body. In this case, it is preferable that the scaffold material for cell culture is coated on a surface of the fiber body, and it is preferable that the scaffold material is a coated material. In the fiber for cell culture, a scaffold material for cell culture may be present in the fiber body. For example, the scaffold material for cell culture can be present in the fiber body by impregnating or kneading the fiber body into a liquid scaffold material for cell culture. In general, the stem cell has a property that is difficult to adhere to a planar structure and easy to adhere to a three-dimensional structure such as a fibrous structure. Therefore, the fiber for cell culture is suitably used for three-dimensional culture of a stem cell. Among the stem cells, an adipose stem cell is more preferably used for three-dimensional culture.

The synthetic resin in the scaffold material for cell culture may be crosslinked. The scaffold material for cell culture containing a crosslinked synthetic resin can effectively suppress a water swelling property and increase the strength. By using a crosslinking agent, the synthetic resin can be crosslinked.

(Cell Culture Container)

The cell culture container according to the present invention includes a container body and the above-mentioned scaffold material for cell culture, and the scaffold material for cell culture is disposed on a surface of the container body.

Figure 1:
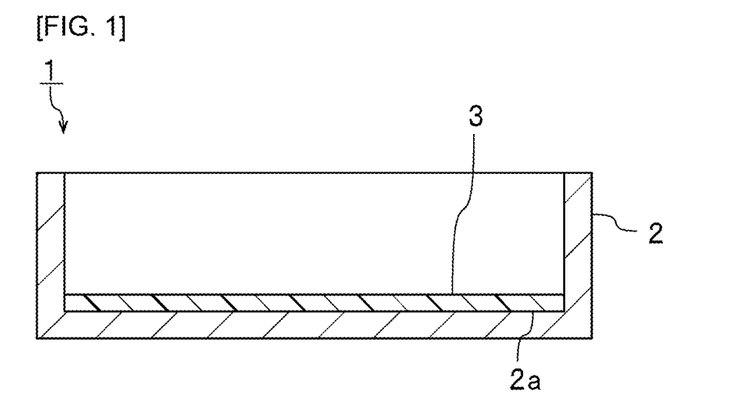
FIG. 1 is a cross-sectional view schematically showing a cell culture container according to an embodiment of the present invention.

FIG. 1 is a cross-sectional view schematically showing a cell culture container according to an embodiment of the present invention.

A cell culture container 1 includes a container body 2 and a scaffold material for cell culture 3. The scaffold material for cell culture 3 is disposed on a surface 2a of the container body 2. The scaffold material for cell culture 3 is disposed on a bottom surface of the container body 2. A cell can be cultured in a plane by adding a liquid medium to the cell culture container 1 and seeding cells such as a cell cluster on a surface of the scaffold material for cell culture 3.

The container body may be provided with a second container body such as a cover glass on a bottom surface of a first container body. The first container body and the second container body may be separable. In this case, the scaffold material for cell culture may be disposed on a surface of the second container body.

As the container body, a conventionally known container body (container) can be used. The shape and size of the container body are not particularly limited.

Examples of the container body include a cell culture plate provided with one or a plurality of wells (holes), and a cell culture flask. The number of wells in the plate is not particularly limited. The number of wells is not particularly limited, and examples thereof include 2, 4, 6, 12, 24, 48, 96, and 384. The shape of the well is not particularly limited, and examples thereof include a perfect circle, an ellipse, a triangle, a square, a rectangle, and a pentagon. The shape of the bottom surface of the well is not particularly limited, and examples thereof include a flat bottom, a round bottom, and uneven bottom. The material of the container body is not particularly limited, and examples thereof include a resin, a metal, and an inorganic material.

EXAMPLES

Hereinafter, the present invention is described in more detail with reference to Examples and Comparative Examples. The present invention is not limited to only these Examples.

The following synthetic resins X1 to X15 and Y1 to Y4 were prepared as materials for a scaffold material for cell culture. Table 1 shows the details of the monomers having a polydentate hydrogen-bonding group used in the synthetic resins X1 to X15.

The content of a structural unit in an obtained synthetic resin was measured by $^1$H-NMR (nuclear magnetic resonance spectrum) after dissolving the synthetic resin in DMSO-d6 (dimethylsulfoxide). Tables 2 to 4 show the content of each structural unit of the synthetic resin. In the table, the content of a polydentate hydrogen-bonding group is the rate of the structural unit having a polydentate hydrogen-bonding group.

Synthetic Resin X1: Synthesis Example X1

To a reactor equipped with a stirrer, 2700 mL of ion-exchanged water, 300 parts by weight of a polyvinyl alcohol having an average degree of polymerization of 250 and a saponification degree of 99 mol % was added, and heated and dissolved while stirring to obtain a solution. To the obtained solution, 35% by weight hydrochloric acid was added as a catalyst so that the hydrochloric acid concentration was 0.2% by weight. The temperature was then adjusted to 15° C. and 22 parts by weight of n-butyraldehyde was added with stirring. Then, 148 parts by weight of n-butyraldehyde was added to precipitate a white particulate polyvinyl butyral resin. Fifteen minutes after the precipitation, 35% by weight hydrochloric acid was added so that the hydrochloric acid concentration was 1.8% by weight, and then the solution was heated to 50° C. and kept at 50° C. for 2 hours. Then, after cooling and neutralizing the solution, the polyvinyl butyral resin was washed with water and dried to obtain a polyvinyl butyral resin (an average degree of polymerization of 250, a degree of acetalization (degree of butyralization) of 71 mol %, a hydroxyl group amount of 28 mol %, and an acetyl group amount of 1 mol %).

Ninety-five parts by weight of the polyvinyl butyral resin was dissolved in tetrahydrofuran so as to be a 20% by weight

TABLE 1

| Formula (1) | Monomer having polydentate hydrogen-bonding group | | Carbon number of R | A1 | A2 | Corresponding formula (2) to (4) |
|---|---|---|---|---|---|---|
| | Structural formula | Name | | | | |
| *—R—(A$_i$)$_n$ (1) | HO—C$_6$H$_3$(OH)—CH$_2$CH$_2$—NH—C(=O)—CH=CH$_2$ | Dopamine acrylamide | 9 | Hydroxyl group | Hydroxyl group | *—R$_1$⟨$^{A_1}_{A_2}$ (2) |
| | B(OH)$_2$—C$_6$H$_4$—NH—C(=O)—C(CH$_3$)=CH$_2$ | 4-methacrylamide phenylboronic acid | 7 | Hydroxyl group | Hydroxyl group | *—R$_1$—R$_2$⟨$^{A_1}_{A_2}$ (3) |
| | H$_2$C=C(CH$_3$)—C(=O)—O—CH$_2$—CH(OH)—CH$_2$OH | Glycerol monomethacrylate | 4 | Hydroxyl group | Hydroxyl group | *—R$_3$⟨$^{A_1}_{A_2}$ (4) |
| | CH$_2$=CH—CH$_2$—CH(NH$_2$)—C(=O)OH | DL-2-allyl-glycine | 2 | Amino group | Carboxyl group | *—R$_3$⟨$^{A_1}_{A_2}$ (4) | solution, 0.1 parts by weight of Irgacure 184 and 5 parts by weight of dopamine acrylamide are added as an initiator, and a synthetic resin X1 was obtained by graft polymerization.

The obtained synthetic resin X1 has a polyvinyl acetal skeleton (polyvinyl butyral skeleton) and a group having a catechol skeleton as a polydentate hydrogen-bonding group. As for the synthetic resin X1, the average degree of polymerization was 250, the hydroxyl group amount in a structural unit having no polydentate hydrogen-bonding group was 38 mol %, the acetyl group amount was 1 mol %, the degree of acetalization was 60 mol %, and the content of polydentate hydrogen-bonding group was 1 mol %.

Synthetic Resin X2: Synthesis Example X2

A synthetic resin X2 was obtained in the same manner as in Synthesis Example X1, except that the amount of polyvinyl butyral resin was changed from 95 parts by weight to 90 parts by weight and the amount of dopamine acrylamide was changed from 5 parts by weight to 10 parts by weight.

The obtained synthetic resin X2 has a polyvinyl acetal skeleton (polyvinyl butyral skeleton) and a group having a catechol skeleton as a polydentate hydrogen-bonding group. As for the synthetic resin X2, the average degree of polymerization was 250, the hydroxyl group amount in a structural unit having no polydentate hydrogen-bonding group was 37 mol %, the acetyl group amount was 1 mol %, the degree of acetalization was 59 mol %, and the content of polydentate hydrogen-bonding group was 3 mol %.

Synthetic Resin X3: Synthesis Example X3

A synthetic resin X3 was obtained in the same manner as in Synthesis Example X1, except that the amount of polyvinyl butyral resin was changed from 95 parts by weight to 80 parts by weight and the amount of dopamine acrylamide was changed from 5 parts by weight to 20 parts by weight.

The obtained synthetic resin X3 has a polyvinyl acetal skeleton (polyvinyl butyral skeleton) and a group having a catechol skeleton as a polydentate hydrogen-bonding group. As for the synthetic resin X3, the average degree of polymerization was 250, the hydroxyl group amount in a structural unit having no polydentate hydrogen-bonding group was 36 mol %, the acetyl group amount was 1 mol %, the degree of acetalization was 57 mol %, and the content of polydentate hydrogen-bonding group was 7 mol %.

Synthetic Resin X4: Synthesis Example X4

A synthetic resin X4 was obtained in the same manner as in Synthesis Example X1, except that the amount of the polyvinyl butyral resin was changed from 95 parts by weight to 90 parts by weight, and 5 parts by weight of dopamine acrylamide and 5 parts by weight of N-(4-hydroxyphenyl) methacrylamide were used for graft polymerization.

The obtained synthetic resin X4 has a polyvinyl acetal skeleton (polyvinyl butyral skeleton) and a group having a catechol skeleton as a polydentate hydrogen-bonding group. As for the synthetic resin X4, the average degree of polymerization was 250, the hydroxyl group amount in a structural unit having no polydentate hydrogen-bonding group was 38 mol %, the acetyl group amount was 1 mol %, the degree of acetalization was 59 mol %, and the content of polydentate hydrogen-bonding group was 2 mol %.

Synthetic Resin X5: Synthesis Example X5

A synthetic resin X5 was obtained in the same manner as in Synthesis Example X1, except that 5 parts by weight of 4-methacrylamide phenylboronic acid was used instead of 5 parts by weight of dopamine acrylamide.

The obtained synthetic resin X5 has a polyvinyl acetal skeleton (polyvinyl butyral skeleton) and a group having a boronic acid skeleton (phenylboronic acid skeleton) as a polydentate hydrogen-bonding group. As for the synthetic resin X5, the average degree of polymerization was 250, the hydroxyl group amount in a structural unit having no polydentate hydrogen-bonding group was 38 mol %, the acetyl group amount was 1 mol %, the degree of acetalization was 60 mol %, and the content of polydentate hydrogen-bonding group was 1 mol %.

Synthetic Resin X6: Synthesis Example X6

A synthetic resin X6 was obtained in the same manner as in Synthesis Example X5, except that the amount of polyvinyl butyral resin was changed from 95 parts by weight to 90 parts by weight and the amount of 4-methacrylamide phenylboronic acid was changed from 5 parts by weight to 10 parts by weight.

The obtained synthetic resin X6 has a polyvinyl acetal skeleton (polyvinyl butyral skeleton) and a group having a boronic acid skeleton (phenylboronic acid skeleton) as a polydentate hydrogen-bonding group. As for the synthetic resin X6, the average degree of polymerization was 250, the hydroxyl group amount in a structural unit having no polydentate hydrogen-bonding group was 37 mol %, the acetyl group amount was 1 mol %, the degree of acetalization was 59 mol %, and the content of polydentate hydrogen-bonding group was 3 mol %.

Synthetic Resin X7: Synthesis Example X7

A synthetic resin X7 was obtained in the same manner as in Synthesis Example X1, except that a polyvinyl butyral resin having an average degree of polymerization of 1700, a degree of butyralization of 63 mol %, a hydroxyl group amount of 34 mol %, and a degree of acetylation of 3 mol % was used.

The obtained synthetic resin X7 has a polyvinyl acetal skeleton (polyvinyl butyral skeleton) and a group having a catechol skeleton as a polydentate hydrogen-bonding group. As for the synthetic resin X7, the average degree of polymerization was 1700, the hydroxyl group amount in a structural unit having no polydentate hydrogen-bonding group was 34 mol %, the acetyl group amount was 3 mol %, the degree of acetalization was 62 mol %, and the content of polydentate hydrogen-bonding group was 1 mol %.

Synthetic Resin X8: Synthesis Example X8

A synthetic resin X8 was obtained in the same manner as in Synthesis Example X7, except that the amount of polyvinyl butyral resin was changed from 95 parts by weight to 90 parts by weight and the amount of dopamine acrylamide was changed from 5 parts by weight to 10 parts by weight.

The obtained synthetic resin X8 has a polyvinyl acetal skeleton (polyvinyl butyral skeleton) and a group having a catechol skeleton as a polydentate hydrogen-bonding group. As for the synthetic resin X8, the average degree of polymerization was 1700, the hydroxyl group amount in a structural unit having no polydentate hydrogen-bonding group was 33 mol %, the acetyl group amount was 3 mol %, the degree of acetalization was 62 mol %, and the content of polydentate hydrogen-bonding group was 2 mol %.

Synthetic Resin X9: Synthesis Example X9

A synthetic resin X9 was obtained in the same manner as in Synthesis Example X7, except that the amount of polyvinyl butyral resin was changed from 95 parts by weight to 80 parts by weight and the amount of dopamine acrylamide was changed from 5 parts by weight to 20 parts by weight.

The obtained synthetic resin X9 has a polyvinyl acetal skeleton (polyvinyl butyral skeleton) and a group having a catechol skeleton as a polydentate hydrogen-bonding group. As for the synthetic resin X9, the average degree of polymerization was 1700, the hydroxyl group amount in a structural unit having no polydentate hydrogen-bonding group was 32 mol %, the acetyl group amount was 3 mol %, the degree of acetalization was 60 mol %, and the content of polydentate hydrogen-bonding group was 5 mol %.

Synthetic Resin X10: Synthesis Example X10

Synthetic resin X10 was obtained in the same manner as in Synthesis Example X7, except that 5 parts by weight of glycerin monomethacrylate was used instead of 5 parts by weight of dopamine acrylamide.

The obtained synthetic resin X10 has a polyvinyl acetal skeleton (polyvinyl butyral skeleton) and a group having an ethylene glycol skeleton as a polydentate hydrogen-bonding group. As for the synthetic resin X10, the average degree of polymerization was 1700, the hydroxyl group amount in a structural unit having no polydentate hydrogen-bonding group was 34 mol %, the acetyl group amount was 3 mol %, the degree of acetalization was 62 mol %, and the content of polydentate hydrogen-bonding group was 1 mol %.

Synthetic Resin X11: Synthesis Example X11

A synthetic resin X11 was obtained in the same manner as in Synthesis Example X10, except that the amount of polyvinyl butyral resin was changed from 95 parts by weight to 90 parts by weight and the amount of glycerin monomethacrylate was changed from 5 parts by weight to 10 parts by weight.

The obtained synthetic resin X11 has a polyvinyl acetal skeleton (polyvinyl butyral skeleton) and a group having an ethylene glycol skeleton as a polydentate hydrogen-bonding group. As for the synthetic resin X11, the average degree of polymerization was 1700, the hydroxyl group amount in a structural unit having no polydentate hydrogen-bonding group was 33 mol %, the acetyl group amount was 3 mol %, the degree of acetalization was 61 mol %, and the content of polydentate hydrogen-bonding group was 3 mol %.

Synthetic Resin X12: Synthesis Example X12

A synthetic resin X12 was obtained in the same manner as in Synthesis Example X7, except that the amount of polyvinyl butyral resin was changed from 95 parts by weight to 80 parts by weight and the amount of glycerin monomethacrylate was changed from 5 parts by weight to 20 parts by weight.

The obtained synthetic resin X12 has a polyvinyl acetal skeleton (polyvinyl butyral skeleton) and a group having an ethylene glycol skeleton as a polydentate hydrogen-bonding group. As for the synthetic resin X12, the average degree of polymerization was 1700, the hydroxyl group amount in a structural unit having no polydentate hydrogen-bonding group was 32 mol %, the acetyl group amount was 3 mol %, the degree of acetalization was 59 mol %, and the content of polydentate hydrogen-bonding group was 6 mol %.

Synthetic Resin X13: Synthesis Example X13

Synthetic resin X13 was obtained in the same manner as in Synthesis Example X11, except that 10 parts by weight of DL-2-allylglycine was changed instead of 10 parts by weight of glycerin monomethacrylate.

The obtained synthetic resin X13 has a polyvinyl acetal skeleton (polyvinyl butyral skeleton), and also has an amino group and a carboxyl group as a polydentate hydrogen-bonding group. As for the synthetic resin X13, the average degree of polymerization was 1700, the hydroxyl group amount in a structural unit having no polydentate hydrogen-bonding group was 33 mol %, the acetyl group amount was 3 mol %, the degree of acetalization was 60 mol %, and the content of polydentate hydrogen-bonding group was 4 mol %.

Synthetic Resin X14: Synthesis Example X14

A synthetic resin X14 was obtained in the same manner as in Synthesis Example X7, except that 5 parts by weight of 4-methacrylamide phenylboronic acid was used instead of 5 parts by weight of dopamine acrylamide.

The obtained synthetic resin X14 has a polyvinyl acetal skeleton (polyvinyl butyral skeleton) and a group having a boronic acid skeleton (phenylboronic acid skeleton) as a polydentate hydrogen-bonding group. As for the synthetic resin X14, the average degree of polymerization was 1700, the hydroxyl group amount in a structural unit having no polydentate hydrogen-bonding group was 33 mol %, the acetyl group amount was 3 mol %, the degree of acetalization was 62 mol %, and the content of polydentate hydrogen-bonding group was 2 mol %.

Synthetic Resin X15: Synthesis Example X15

A synthetic resin X15 was obtained in the same manner as in Synthesis Example X14, except that the amount of polyvinyl butyral resin was changed from 95 parts by weight to 90 parts by weight and the amount of 4-methacrylamide phenylboronic acid was changed from 5 parts by weight to 10 parts by weight.

The obtained synthetic resin X15 has a polyvinyl acetal skeleton (polyvinyl butyral skeleton) and a group having a boronic acid skeleton (phenylboronic acid skeleton) as a polydentate hydrogen-bonding group. As for the synthetic resin X15, the average degree of polymerization was 1700, the hydroxyl group amount in a structural unit having no polydentate hydrogen-bonding group was 33 mol %, the acetyl group amount was 3 mol %, the degree of acetalization was 61 mol %, and the content of polydentate hydrogen-bonding group was 3 mol %.

Synthetic Resin Y1: Synthesis Example Y1

To a reactor equipped with a stirrer, 2700 mL of ion-exchanged water, 300 parts by weight of a polyvinyl alcohol having an average degree of polymerization of 250 and a saponification degree of 99 mol % was added, and heated and dissolved while stirring to obtain a solution. To the obtained solution, 35% by weight hydrochloric acid was added as a catalyst so that the hydrochloric acid concentration was 0.2% by weight. The temperature was then adjusted to 15° C. and 22 parts by weight of n-butyraldehyde was added with stirring. Then, 148 parts by weight of n-butyraldehyde was added to precipitate a white particulate polyvinyl butyral resin. Fifteen minutes after the precipitation, 35% by weight hydrochloric acid was added so that the hydrochloric acid concentration was 1.8% by weight, and then the solution was heated to 50° C. and kept at 50° C. for 2 hours. Then, the solution was cooled and neutralized, and then the polyvinyl butyral resin was washed with water and dried to obtain a synthetic resin Y1 which is a polyvinyl butyral resin.

The obtained synthetic resin Y1 had an average degree of polymerization of 250, a hydroxyl group amount of 57 mol %, an acetyl group amount of 3 mol %, and a degree of acetalization of 40 mol %.

Synthetic Resin Y2: Synthesis Example Y2

The vinyl acetate monomer was dissolved in methanol, and the mixture was stirred at 65° C. for 5 hours while adding an initiator to polymerize. A sodium hydroxide solution (10%) was added to the obtained vinyl acetate polymer solution, and a saponification reaction was carried out for 60 minutes. The obtained product was dried in an oven to obtain a synthetic resin Y2.

The obtained synthetic resin Y2 had an average degree of polymerization of 1000, a hydroxyl group amount of 98 mol %, and an acetyl group amount of 2 mol %.

Synthetic Resin Y3: Synthesis Example Y3

To a reactor equipped with a stirrer, 2700 mL of ion-exchanged water, 300 parts by weight of a polyvinyl alcohol having an average degree of polymerization of 250 and a saponification degree of 99 mol % was added, and heated and dissolved while stirring to obtain a solution. To the obtained solution, 35% by weight hydrochloric acid was added as a catalyst so that the hydrochloric acid concentration was 0.2% by weight. The temperature was then adjusted to 15° C. and 22 parts by weight of n-butyraldehyde was added with stirring. Then, 148 parts by weight of n-butyraldehyde was added to precipitate a white particulate polyvinyl butyral resin. Fifteen minutes after the precipitation, 35% by weight hydrochloric acid was added so that the hydrochloric acid concentration was 1.8% by weight, and then the solution was heated to 50° C. and kept at 50° C. for 2 hours. Then, the solution was cooled and neutralized, and then the polyvinyl butyral resin was washed with water and dried to obtain a synthetic resin Y3.

The obtained synthetic resin Y3 had an average degree of polymerization of 250, a hydroxyl group amount of 28 mol %, an acetyl group amount of 1 mol %, and a degree of acetalization of 71 mol %.

Synthetic Resin Y4: Synthesis Example Y4

To a reactor equipped with a stirrer, 300 parts by weight of a polyvinyl alcohol having an ion-exchanged water of 2700 mL, an average degree of polymerization of 1700 and a saponification degree of 99 mol % was added and dissolved by heating while stirring to obtain a solution. To the obtained solution, 35% by weight hydrochloric acid was added as a catalyst so that the hydrochloric acid concentration was 0.2% by weight. The temperature was then adjusted to 15° C. and 22 parts by weight of n-butyraldehyde was added with stirring. Then, 148 parts by weight of n-butyraldehyde was added to precipitate a white particulate polyvinyl butyral resin. Fifteen minutes after the precipitation, 35% by weight hydrochloric acid was added so that the hydrochloric acid concentration was 1.8% by weight, and then the solution was heated to 50° C. and kept at 50° C. for 2 hours. Then, the solution was cooled and neutralized, and then the polyvinyl butyral resin was washed with water and dried to obtain a synthetic resin Y4 which is a polyvinyl butyral resin.

The obtained synthetic resin Y4 had an average degree of polymerization of 1700, a hydroxyl group amount of 34 mol %, an acetyl group amount of 3 mol %, and a degree of acetalization of 63 mol %.

Examples 1 to 6 and Comparative Examples 1 to 4

Preparation of Cell Culture Container:

One part by weight of the synthetic resin shown in Table 2 was dissolved in 19 parts by weight of butanol. The obtained solution (150 µL) was discharged onto the surface of a cover glass ("22 Maru No. 1" manufactured by Matsunami Glass Ind., Ltd.) that had a diameter of 22 mm and that was dust-removed with an air duster. The cover glass with the discharged solution was rotated at 2000 rpm for 20 seconds using a spin coater, and then heated at 60° C. for 60 minutes to obtain a resin film having a smooth surface (scaffold material for cell culture). A laminated body of the obtained resin film and the cover glass was disposed on a polystyrene dish having a diameter of 22 mm to obtain a cell culture container.

In Comparative Example 1, the polystyrene dish itself was used as a cell culture container.

Seeding and Culturing Cell Cluster:

The following liquid medium and ROCK (Rho-associated kinase)-specific inhibitor were prepared.

TeSR E8 medium (manufactured by STEMCELL Technologies Inc.)

ROCK-Inhibitor (Y27632)

Phosphate buffered saline (1 mL) was added to the obtained cell culture container, the container was allowed to stand in an incubator at 37° C. for 1 hour, and then the phosphate buffered saline was removed from the cell culture container.

A colony of h-iPS cells 252G1 in a confluent state were placed on a dish having a diameter of 35 mm, 1 mL of 0.5 mM ethylenediamine/phosphate buffer solution was added, and the dish was allowed to stand at room temperature for 2 minutes. After removing the ethylenediamine/phosphate buffer solution, pipetting was performed with 1 mL of a liquid medium to obtain a cell cluster crushed to a size of 50 µm to 200 µm. The obtained cell cluster (the number of cells is $1.0 \times 10^5$ cells) was clamp-seeded in the above-mentioned cell culture container.

At the time of seeding, 1.5 mL of the liquid medium and the ROCK-specific inhibitor were added to the cell culture container so that the final concentration was 10 µM. In addition, the cells were cultured in an incubator at 37° C. and a $CO_2$ concentration of 5%. Every 24 hours, 1 mL of the liquid medium was removed, and 1 mL of a fresh liquid medium to which no ROCK-specific inhibitor was added to replace the medium.

(Evaluation)

(1) Cell Cluster Colonization

A photograph was taken under a microscope after medium change every 24 hours after seeding. From the obtained micrographs, the number of days until the seeded cell cluster was detached from the scaffold material for cell culture was confirmed.

<Criteria for Judging of Cell Cluster Colonization>
○○○: Detachment of cell cluster occurs after fifth day from start of culture
○○: Detachment of cell cluster occurs on fourth day from start of culture
○: Detachment of cell cluster occurs on third day from start of culture
x: Detachment of cell cluster occurs on first or second day from start of culture Details and results are shown in Table 2 below.

TABLE 2

|  |  |  | Example 1 | Example 2 | Example 3 | Example 4 | Example 5 | Example 6 |
|---|---|---|---|---|---|---|---|---|
| Polyvinyl acetal resin (before graft polymerization) cr vinyl acetate polymer | Degree of acetalization (degree of butyralization) | mol % | 71 | 71 | 71 | 71 | 71 | 71 |
|  | Acetyl group amount | mol % | 1 | 1 | 1 | 1 | 1 | 1 |
|  | Hydroxyl group amount | mol % | 28 | 28 | 28 | 28 | 28 | 28 |
|  |  | Parts by weight | 95 | 90 | 80 | 90 | 95 | 90 |
| Monomer having polydentate hydrogen-bonding group | Dopamine acrylamide | Parts by weight | 5 | 10 | 20 | 5 | — | — |
|  | 4-methacrylamide phenylboronic acid | Parts by weight | — | — | — | — | 5 | 10 |
| Other monomer | N-(4-hydroxyphenyl) methacrylamide | Parts by weight | — | — | — | 5 | — | — |
| Scaffold materiel for cell culture | Kind | — | Synthetic resin X1 | Synthetic resin X2 | Synthetic resin X3 | Synthetic resin X4 | Synthetic resin X5 | Synthetic resin X6 |
|  | Degree of acetalization (degree of butyralization) | mol % | 60 | 59 | 57 | 59 | 60 | 59 |
|  | Acetyl group amount | mol % | 1 | 1 | 1 | 1 | 1 | 1 |
|  | Hydroxyl group amount in structural unit having no polydentate hydrogen-bonding | mol % | 38 | 37 | 36 | 38 | 38 | 37 |
|  | Content of polydentate hydrogen-bonding group | mol % | 1 | 3 | 7 | 2 | 1 | 3 |
|  | Average degree of polymerization |  | 250 | 250 | 250 | 250 | 250 | 250 |
| Cell cluster colonization | Number of days until cell cluster was detached | Day | 3 | 3 | 3 | 5 | 4 | 4 |
|  |  | Judgement | ○ | ○ | ○ | ○○○ | ○○ | ○○ |

|  |  |  | Comparative Example 1 | Comparative Example 2 | Comparative Example 3 | Comparative Example 4 |
|---|---|---|---|---|---|---|
| Polyvinyl acetal resin (before graft polymerization) cr vinyl acetate polymer | Degree of acetalization (degree of butyralization) | mol % | — | 40 | 0 | 71 |
|  | Acetyl group amount | mol % | — | 3 | 2 | 1 |
|  | Hydroxyl group amount | mol % | — | 57 | 98 | 28 |
|  |  | Parts by weight | — | 100 | 100 | 100 |
| Monomer having polydentate hydrogen-bonding group | Dopamine acrylamide | Parts by weight | — | — | — | — |
|  | 4-methacrylamide phenylboronic acid | Parts by weight | — | — | — | — |
| Other monomer | N-(4-hydroxyphenyl) methacrylamide | Parts by weight | — | — | — | — |
| Scaffold materiel for cell culture | Kind | — | — | Synthetic resin Y1 | Synthetic resin Y2 | Synthetic resin Y3 |
|  | Degree of acetalization (degree of butyralization) | mol % | — | 40 | 0 | 71 |

TABLE 2-continued

|  |  |  |  |  |  |  |
|---|---|---|---|---|---|---|
|  | Acetyl group amount | mol % | — | 3 | 2 | 1 |
|  | Hydroxyl group amount in structural unit having no polydentate hydrogen-bonding | mol % | — | 57 | 98 | 28 |
|  | Content of polydentate hydrogen-bonding group | mol % | — | 0 | 0 | 0 |
|  | Average degree of polymerization |  | — | 250 | 1000 | 250 |
| Cell cluster colonization | Number of days until cell cluster was detached | Day Judgement | 1 x | 1 x | 1 x | 2 x |

Examples 7 to 15 and Comparative Examples 5 to 7

Preparation of Cell Culture Container:

One part by weight of the synthetic resin shown in Tables 3 and 4 was dissolved in 19 parts by weight of butanol. The obtained solution (150 μL) was discharged onto the surface of a cover glass ("22 Maru No. 1" manufactured by Matsunami Glass Ind., Ltd.) that had a diameter of 22 mm and that was dust-removed with an air duster. The cover glass with the discharged solution was rotated at 2000 rpm for 20 seconds using a spin coater, and then heated at 60° C. for 60 minutes to obtain a resin film having a smooth surface (scaffold material for cell culture). A laminated body of the obtained resin film and the cover glass was disposed on a polystyrene dish having a diameter of 22 mm to obtain a cell culture container.

Seeding and Culturing Cell:

The following liquid medium and additives were prepared. MesenCult-ACF Plus 500× Supplement and L-Glutamine 200 mmol/L (100×) were added to MesenCult-ACF Plus Medium which is a liquid medium, so that the final concentration was 1×.

MesenCult-ACF Plus Medium (manufactured by STEMCELL Technologies Inc.)
MesenCult-ACF Plus 500× Supplement (manufactured by STEMCELL Technologies Inc.)
L-Glutamine 200 mmol/L (100×) (manufactured by FUJIFILM Wako Pure Chemical Corporation)

The following cell was prepared as a mesenchymal stem cell (MSC). A marrow stromal cell containing a MSC was conditioned in a medium for MSC, and a cell with a purity of 95% or more for MSC positive markers (CD73, CD90, CD105) and less than 5% for MSC negative markers (CD14, CD34, CD45) was used as a MSC.

Human Bone Marrow Stromal Cells Derived in ACF Medium (manufactured by STEMCELL Technologies Inc.)

Phosphate buffered saline (1 mL) was added to the obtained cell culture container, the container was allowed to stand in an incubator at 37° C. for 1 hour, and then the phosphate buffered saline was removed from the cell culture container.

The MSC in a confluent state was placed on a dish having a diameter of 35 mm, 2 mL of ACF Enzymatic Dissociation Solution (manufactured by STEMCELL Technologies Inc.) was added, and the dish was allowed to stand in an incubator at 37° C. and a $CO_2$ concentration of 5% for 3 minutes. Furthermore, 2 mL of ACF Enzyme Inhibition Solution (manufactured by STEMCELL Technologies Inc.) was added. After centrifugation at 300 rpm for 8 minutes, the supernatant was removed and suspended in a liquid medium to obtain a cell suspension. The obtained cell suspension (the number of cells is $8.0 \times 10^4$ cells) was seeded in the above-mentioned cell culture container.

At the time of seeding, 1.5 mL of the liquid medium was added to the cell culture container. In addition, the cells were cultured in an incubator at 37° C. and a $CO_2$ concentration of 5%.

(Evaluation)

(1) Cell Colonization

Photographs were taken under a microscope 1 day, 3 days, 4 days, and 5 days after seeding. From the obtained micrographs, the number of days that the seeded cells adhered to the scaffold material for cell culture and proliferated was confirmed.

<Criteria for Judging of Cell Colonization>

○○○: Cell adheres on first day from start of culture, and maintains adhesion and proliferation even after fourth day ○○: Cell adheres on first day from start of culture, and maintains adhesion and proliferation until third day ○: Cell adheres on first day from start of culture, and maintains adhesion (does not proliferate) even after third day x: Cell does not adhere and detachment occurs on first day from start of culture.

Details and results are shown in Tables 3 and 4 below.

TABLE 3

|  |  |  | Example 7 | Example 8 | Example 9 | Example 10 | Example 11 | Example 12 |
|---|---|---|---|---|---|---|---|---|
| Polyvinyl acetal resin (before graft polymerization) | Degree of acetalization (degree of butyrailzation) | mol % | 63 | 63 | 63 | 63 | 63 | 63 |
|  | Acetyl group amount | mol % | 3 | 3 | 3 | 3 | 3 | 3 |
|  | Hydroxyl group amount | mol % | 34 | 34 | 34 | 34 | 34 | 34 |
|  |  | Parts by weight | 95 | 90 | 80 | 95 | 90 | 80 |

TABLE 3-continued

|  |  |  | Example 7 | Example 8 | Example 9 | Example 10 | Example 11 | Example 12 |
|---|---|---|---|---|---|---|---|---|
| Monomer having polydentate hydrogen-bonding group | Dopamine acrylamide | Parts by weight | 5 | 10 | 20 | — | — | — |
|  | Glycerol monomethacrylate | Parts by weight | — | — | — | 5 | 10 | 20 |
|  | DL-2-allylglycine | Parts by weight | — | — | — | — | — | — |
|  | 4-methacrylamide phenylboronic acid | Parts by weight | — | — | — | — | — | — |
| Scaffold material for cell culture | Kind | — | Synthetic resin X7 | Synthetic resin X8 | Synthetic resin X9 | Synthetic resin X10 | Synthetic resin X11 | Synthetic resin X12 |
|  | Degree of acetalization (degree of butyralization) | mol % | 62 | 62 | 60 | 62 | 61 | 59 |
|  | Acetyl group amount | mol % | 3 | 3 | 3 | 3 | 3 | 3 |
|  | Hydroxyl group amount in structural unit having no polydentate hydrogen-bonding group | mol % | 34 | 33 | 32 | 34 | 33 | 32 |
|  | Content of polydentate hydrogen-bonding group | mol % | 1 | 2 | 5 | 1 | 3 | 6 |
|  | Average degree of polymerization |  | 1700 | 1700 | 1700 | 1700 | 1700 | 1700 |
| Cell colonization | Number of days to maintain cell adhesion | Day | 5 | 5 | 5 | 5 | 5 | 5 |
|  | Number of days to maintain cell proliferation | Day | 5 | 5 | 5 | 3 | 3 | 3 |
|  | Judgement | — | ○○○ | ○○○ | ○○○ | ○○ | ○○ | ○○ |

TABLE 4

|  |  |  | Example 13 | Example 14 | Example 15 | Comparative Example 5 | Comparative Example 6 | Comparative Example 7 |
|---|---|---|---|---|---|---|---|---|
| Polyvinyl acetal resin (before graft polymerization) | Degree of acetalization (degree of butyralization) | mol % | 63 | 63 | 63 | 63 | 40 | 71 |
|  | acetyl group amount | mol % | 3 | 3 | 3 | 3 | 3 | 1 |
|  | Hydroxyl group amount | mol % | 34 | 34 | 34 | 34 | 57 | 28 |
|  |  | Parts by weight | 95 | 95 | 90 | 100 | 100 | 100 |
| Monomer having polydentate hydrogen-bonding group | Dopamine acrylamide | Parts by weight | — | — | — | — | — | — |
|  | Glycerol monomethacrylate | Parts by weight | — | — | — | — | — | — |
|  | DL-2-allylglycine | Parts by weight | 10 | — | — | — | — | — |
|  | 4-methacrylamide phenylboronic acid | Parts by weight | — | 5 | 10 | — | — | — |
| Scaffold material for cell culture | Kind | — | Synthetic resin X13 | Synthetic resin X14 | Synthetic resin X15 | Synthetic resin Y4 | Synthetic resin Y1 | Synthetic resin Y3 |
|  | Degree of acetalization (degree of butyralization) | mol % | 60 | 62 | 61 | 63 | 40 | 71 |
|  | Acetyl group amount | mol % | 3 | 3 | 3 | 3 | 3 | 1 |
|  | Hydroxyl group amount in structural unit having no polydentate hydrogen-bonding group | mol % | 33 | 33 | 33 | 34 | 57 | 28 |
|  | Content of polydentate hydrogen-bonding group | mol % | 4 | 2 | 3 | 0 | 0 | 0 |
|  | Average degree of polymerization |  | 1700 | 1700 | 1700 | 1700 | 250 | 250 |
| Cell colonization | Number of days to maintain cell adhesion | Day | 3 | 5 | 5 | 1 | 1 | 1 |
|  | Number of days to maintain cell proliferation | Day | 1 | 3 | 3 | — | — | — |
|  | Judgement | — | ○ | ○○ | ○○ | x | x | x |

EXPLANATION OF SYMBOLS

1: Cell culture container
2: Container body
2a: Surface
3: Scaffold material for cell culture
10: Cell
11: Substance capable of forming hydrogen bonds
20: Scaffold material for cell culture
30: Hydrogen bond

The invention claimed is:

1. A scaffold material for cell culture comprising a synthetic resin having a main chain and a graft chain,
the graft chain having a polydentate hydrogen-bonding group represented by the following formula (1) in a side chain:

[Chemical 1]

$$*-R-(A_i)_n \quad (1)$$

wherein R represents a group having 50 or less carbon atoms, $A_i$ represents an amino group, a carboxyl group, a hydroxyl group, a sulfone group, an imino group, or a thiol group, i represents a natural number, n represents an integer of two or more and four or less, and * represents a bonding position with another atom constituting the graft chain; and $A_i$ may be identical or different from each other, and
wherein a rate of a structural unit having the polydentate hydrogen-bonding group to 100 mol % of all structural units of the synthetic resin is 1 mol % or more and 30 mol % or less.

2. The scaffold material for cell culture according to claim 1, wherein
the polydentate hydrogen-bonding group is a polydentate hydrogen-bonding group represented by the following formula (2), the following formula (3), or the following formula (4):

[Chemical 2]

$$*-R_1{\overset{A_1}{\underset{A_2}{\diagup\!\!\!\diagdown}}} \quad (2)$$

wherein $R_1$ represents a group having a cyclic skeleton and having 50 or less carbon atoms, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other,

[Chemical 3]

$$*-R_1-R_2{\overset{A_1}{\underset{A_2}{\diagup\!\!\!\diagdown}}} \quad (3)$$

wherein $R_1$ represents a group having a cyclic skeleton and having 50 or less carbon atoms, $R_2$ represents a boron atom, a phosphorus atom, a silicon atom, a nitrogen atom, or a metal atom, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other,

[Chemical 4]

$$*-R_3{\overset{A_1}{\underset{A_2}{\diagup\!\!\!\diagdown}}} \quad (4)$$

wherein $R_3$ represents a group having a chain skeleton and having 50 or less carbon atoms, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other.

3. The scaffold material for cell culture according to claim 2, wherein the polydentate hydrogen-bonding group is a polydentate hydrogen-bonding group represented by the formula (2) or the formula (3).

4. The scaffold material for cell culture according to claim 1, wherein the polydentate hydrogen-bonding group has two or more functional groups of at least one kind selected from the group consisting of an amino group, a carboxyl group, and a hydroxyl group.

5. The scaffold material for cell culture according to claim 1, wherein the polydentate hydrogen-bonding group has at least one skeleton selected from the group consisting of a catechol skeleton, a phenylenediamine skeleton, a phenylboronic acid skeleton, a naphthaleneboronic acid skeleton, a glycerol skeleton, an ethylene glycol skeleton, and a glycine derivative skeleton.

6. The scaffold material for cell culture according to claim 1, which does not substantially contain an animal-derived raw material.

7. The scaffold material for cell culture according to claim 1, wherein the synthetic resin is a polyvinyl alcohol derivative or a poly(meth)acrylic ester derivative.

8. The scaffold material for cell culture according to claim 1, wherein the synthetic resin has a polyvinyl acetal skeleton or a poly(meth)acrylic ester skeleton.

9. The scaffold material for cell culture according to claim 1, wherein the synthetic resin has a polyvinyl acetal skeleton.

10. A cell culture container comprising:
a container body; and
the scaffold material for cell culture according to claim 1, the scaffold material for cell culture being disposed on a surface of the container body.

11. A scaffold material for cell culture comprising a synthetic resin having a main chain and a graft chain,
the graft chain having a polydentate hydrogen-bonding group represented by the following formula (1) in a side chain:

[Chemical 1]

$$*-R-(A_i)_n \quad (1)$$

wherein R represents a group having 50 or less carbon atoms, $A_i$ represents an amino group, a carboxyl group, a hydroxyl group, a sulfone group, an imino group, or a thiol group, i represents a natural number, n represents an integer of two or more and four or less, and * represents a bonding position with another atom constituting the graft chain; and $A_i$ may be identical or different from each other, and wherein the polydentate hydrogen-bonding group has at least one skeleton selected from the group consisting of a catechol skeleton, a phenylenediamine skeleton, a phenylboronic acid skeleton, a naphthaleneboronic acid skeleton, a glycerol skeleton, an ethylene glycol skeleton, and a glycine derivative skeleton.

12. The scaffold material for cell culture according to claim 11, wherein
the polydentate hydrogen-bonding group is a polydentate hydrogen-bonding group represented by the following formula (2), the following formula (3), or the following formula (4):

[Chemical 2]

(2)

wherein $R_1$ represents a group having a cyclic skeleton and having 50 or less carbon atoms, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other,

[Chemical 3]

(3)

wherein $R_1$ represents a group having a cyclic skeleton and having 50 or less carbon atoms, $R_2$ represents a boron atom, a phosphorus atom, a silicon atom, a nitrogen atom, or a metal atom, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other,

[Chemical 4]

(4)

wherein $R_3$ represents a group having a chain skeleton and having 50 or less carbon atoms, $A_1$ and $A_2$ represent an amino group, a carboxyl group, a hydroxyl group, a sulfone group, an imino group, or a thiol group, respectively, and * represents a bonding site with another atom constituting the graft chain; and $A_1$ and $A_2$ may be identical or different from each other.

13. The scaffold material for cell culture according to claim 12, wherein the polydentate hydrogen-bonding group is a polydentate hydrogen-bonding group represented by the formula (2) or the formula (3).

14. The scaffold material for cell culture according to claim 11, wherein the polydentate hydrogen-bonding group has two or more functional groups of at least one kind selected from the group consisting of an amino group, a carboxyl group, and a hydroxyl group.

15. The scaffold material for cell culture according to claim 11, which does not substantially contain an animal-derived raw material.

16. The scaffold material for cell culture according to claim 11, wherein the synthetic resin is a polyvinyl alcohol derivative or a poly(meth)acrylic ester derivative.

17. The scaffold material for cell culture according to claim 11, wherein the synthetic resin has a polyvinyl acetal skeleton or a poly(meth)acrylic ester skeleton.

18. The scaffold material for cell culture according to claim 11, wherein the synthetic resin has a polyvinyl acetal skeleton.

19. A cell culture container comprising:
a container body; and
the scaffold material for cell culture according to claim 12,
the scaffold material for cell culture being disposed on a surface of the container body.

* * * * *